US00PP09914P

United States Patent [19]

Rabb

[11] Patent Number: Plant 9,914

[45] Date of Patent: Jun. 3, 1997

[54] CHRYSANTHEMUM PLANT NAMED 'CHERRY DAVIS'

[76] Inventor: Frederick H. Rabb, Box 21, Site 14, RR1, Strathmore, Alberta, Canada, T1P 1J6

[21] Appl. No.: 632,132

[22] Filed: Apr. 15, 1996

[51] Int. Cl.[6] ..... A01H 5/00

[52] U.S. Cl. ..... Plt./82.5

[58] Field of Search ..... Plt./74.1, 82.4, Plt./82.5

[56] References Cited

U.S. PATENT DOCUMENTS

| | | | |
|---|---|---|---|
| P.P. 7,325 | 9/1990 | VandenBerg | Plt./82.5 |
| P.P. 8,097 | 1/1993 | VandenBerg | Plt./82.4 |
| P.P. 8,292 | 7/1993 | VandenBerg | Plt./74.1 |
| P.P. 8,293 | 7/1993 | VandenBerg | Plt./74.1 |

*Primary Examiner*—Howard J. Locker
*Attorney, Agent, or Firm*—Foley & Lardner

[57] ABSTRACT

A Chrysanthemum plant named Cherry Davis particularly characterized by its flat capitulum form; daisy capitulum type; cherry-red ray floret color; diameter across face of capitulum of 64 to 70 mm when fully opened, when grown as a pinched spray pot mum; photoperiodic flowering response to short days of 54 to 60 days; plant height, with 14 to 16 long days after sticking unrooted cuttings and with 1 to 3 applications of 2500 ppm B-9 SP, ranges from 23 to 28 cm when grown as a pinched pot mum with 4 cuttings in a 15 cm pot; branching pattern is spreading, each plant developing 4 to 6 laterals after pinch; and recommended as a spray pot mum.

1 Drawing Sheet

The present invention comprises a new and distinct cultivar of chrysanthemum, botanically known as *Dendranthema grandiflora*, and referred to by the cultivar name Cherry Davis.

Cherry Davis, identified as 6831 (93-#02237) is a spontaneous mutation of the cultivar Regal Davis, disclosed in U.S. Plant Pat. No. 8,292, and was selected to expand the color range of the parental variety.

Cherry Davis was discovered and selected by inventor Frederick H. Rabb as one flowering plant within a flowering block of Regal Davis in August of 1993 in a controlled environment in Strathmore, Alberta, Canada.

The first act of asexual reproduction of Cherry Davis was accomplished when vegetative cuttings were taken from the initial selection in November of 1993 in a controlled environment in Strathmore, Alberta, Canada, by Frederick H. Rabb.

Horticultural examination of controlled flowerings of successive plantings has shown that the unique combination of characteristics as herein disclosed for Cherry Davis are firmly fixed and are retained through successive generations of asexual reproduction.

Cherry Davis has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Cherry Davis, which, in combination, distinguish this Chrysanthemum as a new and distinct cultivar:

1. Flat capitulum form.
2. Daisy capitulum type.
3. Cherry-red ray floret color.
4. Diameter across face of capitulum of 64 to 70 mm when fully opened, when grown as a pinched spray pot mum.
5. Photoperiodic flowering response to short days of 54 to 60 days.

6. Plant height, with 14 to 16 long days after sticking unrooted cuttings and with 1 to 3 applications of 2500 ppm B–9 SP, ranges from 23 to 28 cm when grown as a pinched pot mum with 4 cuttings in a 15 cm pot.
7. Branching pattern is spreading, each plant developing 4 to 6 laterals after pinch.
8. Recommended as a spray pot mum.

The accompanying photographic drawing is a side view of a potted mum of Cherry Davis, with 4 cuttings in a 15 cm pot, with the colors being as nearly true as possible with illustrations of this type.

Of the commercial cultivars known to the inventor, the most similar in comparison to Cherry Davis is the cultivar Coral Davis, disclosed in U.S. Plant Pat. No. 8,097. All traits of Cherry Davis are similar to those of Coral Davis, except for the ray floret color. The ray floret color of Cherry Davis is significantly darker (R.H.S. 51A to 54A) than the ray floret color of Coral Davis (R.H.S. 51C to 54C, tinged with 185D).

In the following description color references are made to The Royal Horticultural Society Colour Chart. The color values were determined on plant material grown as a pinched disbudded pot mum in Salinas, Calif. on May 22, 1995.

Classification:

*Botanical.*—*Dendranthema grandiflora* cv Cherry Davis.

*Commercial.*—Flat daisy spray pot mum.

INFLORESCENCE

A. Capitulum:

*Form.*—Flat.

*Type.*—Daisy.

*Diameter across face.*—64 to 70 mm when fully opened.

B. Corolla of ray florets:

*Color (general tonality from a distance of three meters)*.—Cherry-red.

*Color (upper surface)*.—51A to 54A.

*Color* (*under surface*).—51B to 51C.
*Shape*.—Flat, straight, slightly ribbed.

C. Corolla of disc florets:
*Color* (*mature*).—9A.
*Color* (*immature*).—144B.

D. Reproductive organs:
*Androecium*.—Present on disc florets only; no pollen.
*Gynoecium*.—Present on both ray and disc florets.

PLANT

General appearance:
*Height*.—23 to 28 cm when grown as a pinched pot mum with 14 to 16 long days after sticking unrooted cuttings prior to start of short days, with 1 to 3 applications of 2500 ppm B–9 SP.
*Branching pattern*.—Spreading, each plant developing 4 to 6 laterals after pinch.

Foliage:
*Color* (*upper surface*).—147A.
*Color* (*under surface*).—147B.
*Shape*.—Deeply lobed and serrated.

What is claimed is:

1. A new and distinct Chrysanthemum plant named Cherry Davis, as described and illustrated.

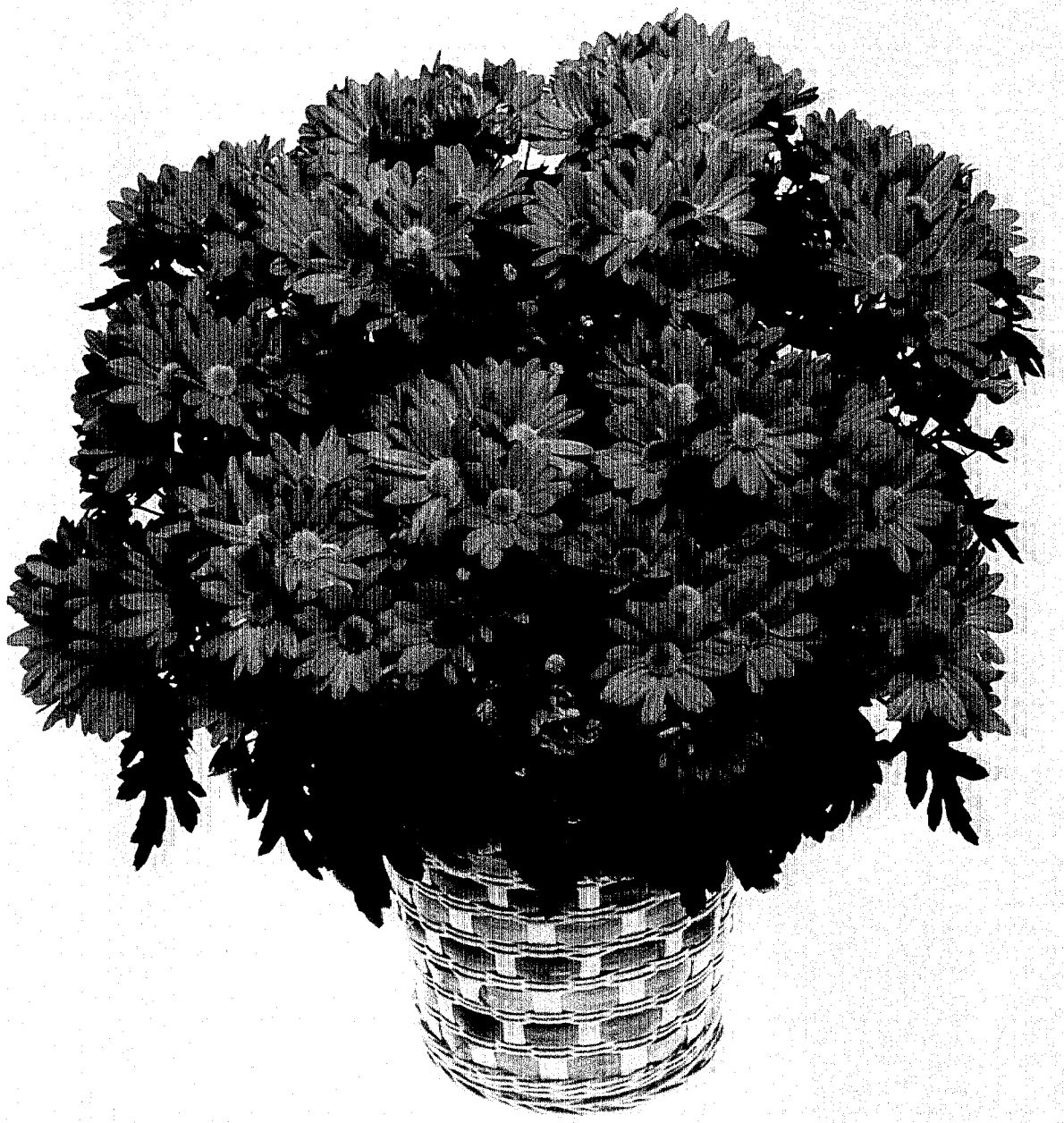

* * * * *